(12) United States Patent
Gerber

(10) Patent No.: US 11,167,070 B2
(45) Date of Patent: Nov. 9, 2021

(54) GANGED MODULAR RECHARGING SYSTEM

(71) Applicant: Medtronic, Inc., Minneapolis, MN (US)

(72) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1009 days.

(21) Appl. No.: 15/831,530

(22) Filed: Dec. 5, 2017

(65) Prior Publication Data

US 2018/0214623 A1 Aug. 2, 2018

Related U.S. Application Data

(60) Provisional application No. 62/451,940, filed on Jan. 30, 2017.

(51) Int. Cl.
*B01J 20/22* (2006.01)
*A61M 1/16* (2006.01)
*B01J 20/34* (2006.01)
*B01J 20/20* (2006.01)
*B01D 15/20* (2006.01)
*B01J 20/02* (2006.01)

(52) U.S. Cl.
CPC ......... *A61M 1/1696* (2013.01); *B01D 15/203* (2013.01); *B01J 20/0211* (2013.01); *B01J 20/0292* (2013.01); *B01J 20/20* (2013.01); *B01J 20/3416* (2013.01); *B01J 20/3433* (2013.01); *B01J 20/3475* (2013.01)

(58) Field of Classification Search
CPC ............ B01J 20/22; B01J 41/16; B01D 15/22
USPC ....................................................... 502/402
See application file for complete search history.

(56) References Cited

U.S. PATENT DOCUMENTS

| | | |
|---|---|---|
| 1,617,288 A | 2/1927 | Kenney |
| 3,608,729 A | 9/1971 | Haselden |
| 3,617,558 A | 11/1971 | Jones |
| 3,669,880 A | 6/1972 | Marantz et al. |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen et al. |
| 3,989,622 A | 11/1976 | Marantz |
| 4,073,725 A | 2/1978 | Takeuchi |
| 4,094,775 A | 6/1978 | Mueller |
| 4,192,748 A | 3/1980 | Hyden |
| 4,206,054 A | 6/1980 | Moore |
| 4,209,392 A | 6/1980 | Wallace |
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,661,246 A | 4/1987 | Ash |
| 4,684,460 A | 8/1987 | Issautier |
| 4,687,582 A | 8/1987 | Dixon |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson |
| 5,858,186 A | 1/1999 | Glass |
| 5,944,684 A | 8/1999 | Roberts et al. |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor et al. |
| 7,276,042 B2 | 10/2007 | Polaschegg et al. |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi et al. |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

Chinese Office Action for App. No. 201711179528.X, dated Jul. 27, 2020.

(Continued)

*Primary Examiner* — Edward M Johnson

(57) ABSTRACT

The invention relates to systems and methods for recharging sorbent materials and other rechargeable dialysis components. The systems and methods include rechargers, flow paths, and related components for connecting multiple rechargers together to sharing infrastructure and resources. The rechargeable dialysis components can include zirconium phosphate, zirconium oxide, and other sorbent cartridge materials including any combination thereof or any other rechargeable component of a dialysis system. Additionally, a single-use cartridge or a multi-use cartridge can be used in the present invention.

17 Claims, 8 Drawing Sheets

(56) References Cited

U.S. PATENT DOCUMENTS

| | | |
|---|---|---|
| 7,794,419 B2 | 7/2010 | Paolini et al. |
| 7,776,210 B2 | 8/2010 | Rosenbaum et al. |
| 7,850,635 B2 | 12/2010 | Polaschegg et al. |
| 7,922,686 B2 | 4/2011 | Childers et al. |
| 7,922,911 B2 | 4/2011 | Micheli |
| 7,947,179 B2 | 5/2011 | Rosenbaum et al. |
| 7,955,290 B2 | 6/2011 | Karoor et al. |
| 7,988,854 B2 | 8/2011 | Tsukamoto |
| 8,002,726 B2 | 8/2011 | Karoor et al. |
| 8,012,118 B2 | 9/2011 | Curtin |
| 8,029,454 B2 | 11/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Hamada et al. |
| 8,404,491 B2 | 3/2013 | Ding et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2002/0016550 A1 | 2/2002 | Sweeney |
| 2002/0112609 A1 | 8/2002 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0168963 A1 | 9/2004 | King |
| 2004/0257409 A1 | 12/2004 | Cheok |
| 2005/0006296 A1 | 1/2005 | Sullivan |
| 2005/0056592 A1 | 3/2005 | Braunger |
| 2005/0113796 A1 | 5/2005 | Taylor |
| 2005/0150832 A1 | 7/2005 | Tsukamoto |
| 2005/0234354 A1 | 10/2005 | Rowlandson |
| 2005/0274658 A1 | 12/2005 | Rosenbaum |
| 2006/0241543 A1 | 10/2006 | Gura |
| 2007/0007208 A1 | 1/2007 | Brugger et al. |
| 2007/0179431 A1 | 8/2007 | Roberts et al. |
| 2007/0213665 A1 | 9/2007 | Curtin et al. |
| 2008/0006570 A1 | 1/2008 | Gura |
| 2008/0011664 A1 | 1/2008 | Karoor |
| 2008/0051696 A1 | 2/2008 | Curtin |
| 2008/0053905 A9 | 3/2008 | Brugger et al. |
| 2008/0241031 A1 | 10/2008 | Li |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0216045 A1 | 8/2009 | Singh |
| 2009/0266358 A1 | 10/2009 | Sacristan Rock |
| 2009/0282980 A1 | 11/2009 | Gura |
| 2010/0004588 A1 | 1/2010 | Yeh et al. |
| 2010/0007838 A1 | 1/2010 | Fujimoto |
| 2010/0078381 A1 | 4/2010 | Merchant |
| 2010/0078387 A1 | 4/2010 | Wong |
| 2010/0084330 A1 | 4/2010 | Wong |
| 2010/0100027 A1 | 4/2010 | Schilthuizen et al. |
| 2010/0101195 A1 | 4/2010 | Clements |
| 2010/0102190 A1 | 4/2010 | Zhu et al. |
| 2010/0114012 A1 | 5/2010 | Sandford et al. |
| 2010/0217181 A1 | 8/2010 | Roberts et al. |
| 2010/0224492 A1 | 9/2010 | Ding et al. |
| 2010/0312172 A1 | 12/2010 | Hoffman |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2012/0273354 A1 | 11/2012 | Orhan et al. |
| 2012/0303079 A1 | 11/2012 | Mahajan |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0158588 A1 | 6/2014 | Pudil |
| 2014/0158623 A1 | 6/2014 | Pudil |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108069 A1 | 4/2015 | Merchant |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243540 A1 | 8/2016 | Menon |
| 2016/0243541 A1 | 8/2016 | Menon |
| 2018/0221852 A1 | 8/2018 | Pudil |

FOREIGN PATENT DOCUMENTS

| | | |
|---|---|---|
| CN | 105658326 A | 6/2016 |
| CN | 106413878 A | 2/2017 |
| EP | 711182 B1 | 6/2003 |
| EP | 1592494 B1 | 6/2009 |
| EP | 2575827 A2 | 12/2010 |
| EP | 2576453 A2 | 12/2011 |
| EP | 2446908 | 5/2012 |
| EP | 1545652 B1 | 1/2013 |
| EP | 1345856 B1 | 3/2013 |
| EP | 2344220 B1 | 4/2013 |
| EP | 3546042 | 10/2019 |
| EP | 3626280 | 3/2020 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2007-44602 A | 2/2007 |
| JP | 200744602 | 2/2007 |

(56) References Cited

FOREIGN PATENT DOCUMENTS

| | | |
|---|---|---|
| JP | 200744602 A | 2/2007 |
| JP | 2013502987 | 10/2013 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | WO 2003041764 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | 2008075951 A1 | 6/2008 |
| WO | 2009157877 A1 | 12/2009 |
| WO | 2009157878 A1 | 12/2009 |
| WO | 20090157877 | 12/2009 |
| WO | 2010028860 A1 | 3/2010 |
| WO | 2010102190 A4 | 11/2010 |
| WO | 2010141949 | 12/2010 |
| WO | WO 2011/017215 | 2/2011 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 A3 | 2/2013 |
| WO | WO 2013/019179 | 2/2013 |
| WO | WO 2013/019994 | 2/2013 |
| WO | WO 2013-025957 | 2/2013 |
| WO | WO 2013-028809 | 2/2013 |
| WO | WO 2013019179 | 2/2013 |
| WO | WO2014121238 A1 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2015060914 | 4/2015 |
| WO | WO 2015060914 | 4/2015 |
| WO | WO 2015/126879 | 8/2015 |
| WO | 2015142624 | 9/2015 |
| WO | 2015199764 | 9/2015 |
| WO | 2015-199863 | 12/2015 |
| WO | 2015-199864 | 12/2015 |
| WO | 2015199765 | 12/2015 |
| WO | 2015199863 | 12/2015 |
| WO | 2015199864 | 12/2015 |
| WO | WO 2015199765 | 12/2015 |
| WO | WO 2016/191039 | 12/2016 |
| WO | WO 2016/191041 | 12/2016 |

OTHER PUBLICATIONS

Office Action for Chinese App. No. 201810042927, dated Sep. 23, 2019.
European Search Report for App. No. 18153940.4, dated Jun. 12, 2018.
European Search Report for App. No. 18153940.4, dated Sep. 28, 2018.
European Search Report for App. No. 20164524.9, dated Aug. 21, 2020.
European Search Report for App. No. 20158130.3, dated Jul. 8, 2020.
Search Report in EP App. No. 15752771, dated Nov. 22, 2017.
PCT/US2016/030319_IPRP.
Office Action in Japanese Application No. 2016-553344, dated Apr. 24, 2018.
European Search Report for App. No. 15812081.6, dated Mar. 8, 2018.
European Search Report App 14865374.4, dated Jun. 12, 2017.
PCT/US2015/032485 Written Opinion dated Oct. 16, 2015.
PCT/US2015/032485 Written Opinion dated May 9, 2016.
PCT/US15/18587 International Preliminary Report on Patentability dated Jun. 6, 2016.
PCT/US2016/030304_IPRP.
PCT/US2015/020044 International Search Report Written Opinion dated Jun. 30, 2015.
PCT/US2015/020046 International Search Report and Written Opinion dated Jun. 29, 2015.
European Search Report and Supplemental Search Report in European Application No. 14865374.4 dated Jun. 12, 2017.
PCT/US2015/032494 International Preliminary Report on Patentablity dated Dec. 27, 2016.
PCT/US2015/019901 International Preliminary Report on Patentability dated May 27, 2016.
PCT/US2015/019901 International Search Report and Written Opinion dated Jun. 5, 2015.
PCT/US2015/032492 Written Opinion dated Nov. 19, 2015.
PCT/US2016/030320 International Preliminary Report on Patentability, dated Apr. 20, 2017.
PCT/US2015/032485 International Search Report and Written Opinion dated Oct. 16, 2015.
PCT/US2015/032485 Written Opinion dated Oct. 16, 2016.
PCT/US2016/030320 International Search Report dated Jul. 28, 2016.
PCT/US2016/030320 Written Opinion dated Jul. 28, 2016.
PCT/US2016/030319 Written Opinion dated Jul. 27, 2016.
PCT/US2016/030319 International Search Report dated Jul. 27, 2016.
PCT/US2016/030312 International Search Report dated Jul. 28, 2016.
PCT/US2016/030312 Written Opinion dated Jul. 28, 2016.
PCT/US2016/030304 Written Opinion dated Jul. 27, 2016.
PCT/US2016/030304 International Search Report dated Jul. 27, 2016.
PCT/US20115/032485 International Preliminary Report on Patentability dated May 11, 2016.
PCT/US2015/032485 International Preliminary Report on Patentability dated May 11, 2016.
PCT/US2015/019901 International Search Report dated Jun. 5, 2015.
PCT/US2015/019901 Written Opinion dated Jun. 5, 2015.
PCT/US2015/019901 Written Opinion dated May 27, 2016.
PCT/US2015/032494 International Search Report dated Nov. 19, 2015.
PCT/US2015/032494 Written Opinion dated Nov. 19, 2015.
Office Action in App. No. JP 2016-515476 dated Dec. 26, 2016.
Wester et al., A regenerable postassium and phosphate sorbent system to enhance dialysis efficacy and device portability: an in vitro study Nephrol Dial Transplant (2013) 28: 2364-2371 Jul. 3, 2013.
PCT/US2015/016273 International Search Report and Written Opinion dated Jun. 9, 2015.
PCT/US2016/030320 Written Opinion dated Jul. 27, 2016.
Office Action in App. No. AU 2015280604 dated Apr. 8, 2016.
PCT/US2015/016270 International Search Report and Written Opinion dated Jun. 5, 2015.
John Wm Agar: Review: Understanding sorbent dialysis systems, Nephrology, vol. 15, No. 4, Jun. 1, 2010, pp. 406-411.
PCT/US2015/032492 International Search Report dated Nov. 19, 2015.
U.S. Appl. No. 13/835,735, filed Mar. 15, 2013.
U.S. Appl. No. 14/240,129, filed Aug. 22, 2013.
U.S. Appl. No. 13/836,079, filed Mar. 15, 2013.
U.S. Appl. No. 13/757,693, filed Jan. 4, 2013.
U.S. Appl. No. 14/259,589, filed Apr. 23, 2014.
U.S. Appl. No. 14/259,655, filed Apr. 23, 2014.
U.S. Appl. No. 13/836,973, filed Mar. 15, 2013.
PCT Application, PCT/US20013/020404, filed Jan. 4, 2013.
PCT/US2014/065950 International Search Report and Written Opinion dated Feb. 24, 2015.
U.S. Appl. No. 61/526,209.

(56) References Cited

OTHER PUBLICATIONS

International Search Report from PCT/US2012/051946 dated Mar. 4, 2013.
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
Japanese Patent Publication No. S50-70281A.
European Search Report for EP App. No. 15811326.6, dated Feb. 14, 2018.
European Search Report for EP App. No. 15812413.1, dated Feb. 2, 2018.
Search Report for EP App. No. 17203984.4, dated Mar. 29, 2018.
Chinese Office Action for App. No. 201810580243.5, dated Jul. 3, 2020.

GANGED MODULAR RECHARGING SYSTEM

CROSS-REFERENCE TO RELATED APPLICATIONS

This application claims the benefit of and priority to U.S. Provisional Patent Application No. 62/451,940 filed Jan. 30, 2017, the entire disclosure of which is incorporated by reference herein.

FIELD OF THE INVENTION

The invention relates to systems and methods for recharging sorbent materials and other rechargeable dialysis components. The systems and methods include rechargers, flow paths, and related components for connecting multiple rechargers together to sharing infrastructure and resources. The rechargeable dialysis components can include zirconium phosphate, zirconium oxide, and other sorbent cartridge materials including any combination thereof or any other rechargeable component of a dialysis system. Additionally, a single-use cartridge or a multi-use cartridge can be used in the present invention.

BACKGROUND

Zirconium phosphate and zirconium oxide are used in sorbent dialysis to remove waste and unwanted solutes from spent dialysate. Usually, sorbent cartridges are discarded and replaced after use. The discarded sorbent cartridges are broken down and the individual materials separated from each other. Zirconium phosphate is a sorbent material that removes ammonium, potassium, calcium, and magnesium ions from dialysate and zirconium oxide is a sorbent material that removes anions such as phosphate or fluoride ions. Both materials are usually packaged together in a cartridge or packed in separate cartridges. Because zirconium phosphate and zirconium oxide are expensive and rechargeable, sorbent re-processers treat the recovered zirconium phosphate and zirconium oxide with a series of chemical solutions. The recycling process requires transporting the materials to reprocessing facilities and involves laborious recycling steps in addition to recharging the sorbent materials. Further, the sorbent material cannot be immediately reused, and must be added to a new sorbent cartridge and repackaged for sale. Safe disposal of the chemical waste from solutions used to recharge the materials can also require additional steps such as neutralizing the recharging solutions. Conventional methods drive up costs and infrastructure requirements, and increase complexity and waste.

Hence, there is a need for systems and methods that can recharge sorbent materials and other dialysis components while still in the sorbent cartridges. The need includes recharging one to a large number of sorbent cartridges or components. The need includes recharging various types of sorbent materials either independently or separately. The need further includes systems and methods for sorbent recharging at lower costs and reduced complexity. The need can include multiple rechargers being connected together to facilitate sharing of infrastructure and resources. The need includes recharging single-use sorbent cartridges and/or multi-use sorbent cartridges. The need extends to systems and methods for recharging sorbent materials in separate rechargers, either simultaneously or separately, while requiring only a single set of recharging solutions.

SUMMARY OF THE INVENTION

The first aspect of the invention is drawn to a recharger. The recharger can have at least one recharger connector affixed to an outer surface of the recharger and fluidly connectable to a fluid line or a second recharger; wherein the recharger connector is fluidly connected to at least one recharging flow path.

In any embodiment, the recharging flow path can be selected from: a zirconium phosphate recharging flow path having a zirconium phosphate module inlet and a zirconium phosphate module outlet, a zirconium oxide recharging flow path having a zirconium oxide module inlet and zirconium oxide module outlet, an activated carbon recharging flow path comprising an activated carbon module inlet and an activated carbon module outlet, an alumina recharging flow path comprising an alumina module inlet and an alumina module outlet, and combinations thereof.

In any embodiment, the recharger connector can be fluidly connectable to a first end of a fluid connector; and a second end of the fluid connector can be fluidly connectable to a recharger connector of a second recharger.

In any embodiment, the recharger can have a zirconium phosphate recharging flow path having a zirconium phosphate module inlet and a zirconium phosphate module outlet and a zirconium oxide recharging flow path having a zirconium oxide module inlet and zirconium oxide module outlet; and a drain line fluidly connectable to one or both of the zirconium phosphate module outlet and zirconium oxide module outlet.

In any embodiment, the drain line can be fluidly connectable to a drain line of a second recharger.

In any embodiment, the drain line can be fluidly connectable to a common reservoir; and the common reservoir can be fluidly connectable to a drain line of a second recharger.

In any embodiment, the recharger can have multiple recharger connectors.

In any embodiment, the recharger connector can be fastened to a recharger connector of a second recharger.

Any of the features disclosed as being part of the first aspect of the invention can be included in the first aspect of the invention, either alone or in combination.

The second aspect of the invention is drawn to a recharging system. The recharging system can include at least one recharger having at least one receiving compartment for receiving a rechargeable dialysis component; at least one inlet and outlet; the inlet fluidly connectable to a recharging flow path; the recharger in fluid communication with a fluid line; at least one recharging solution source selected from the group consisting of a disinfectant source, a water source, a brine source, a base source, and an acid source; the recharging solution source fluidly connected to a fluid line; the recharging solution source in fluid communication with the fluid line; and at least one recharger connector affixed to an outer surface of the recharger, the recharger connector in fluid communication with the fluid line.

In any embodiment, the recharging system can include a second recharger connector affixed to an outer surface of the recharger; the second recharger connector fluidly connectable to a recharger connector of a second recharger.

In any embodiment, the second recharger connector can be directly connectable to the recharger connector of the second recharger.

In any embodiment, the second recharger connector can be fluidly connectable to a fluid line; the fluid line fluidly connectable to the recharger connector of the second recharger.

In any embodiment, the fluid line can be fluidly connectable to both a zirconium phosphate recharging flow path and a zirconium oxide recharging flow path.

In any embodiment, the fluid line can have at least two recharger connectors, each of the at least two recharger connectors fluidly connectable to a recharger.

In any embodiment, the recharger connector can be a sealable connector; wherein the recharger connector is sealed and/or fluidly connected to the second recharger.

In any embodiment, the recharging system can have a drain line fluidly connected to at least a first recharger and a second recharger.

In any embodiment, the drain line can be fluidly connected to a drain.

In any embodiment, the drain line can be fluidly connected to a common reservoir.

Any of the features disclosed as being part of the second aspect of the invention can be included in the second aspect of the invention, either alone or in combination.

The third aspect of the invention is drawn to a method of recharging a sorbent material in a reusable sorbent module. In any embodiment, the method can include connecting a sorbent module containing the sorbent material to a module inlet and a module outlet in a first recharger; wherein the module inlet and module outlets are fluidly connected to a first recharging flow path; connecting the first recharging flow path to a recharging solution source through a first recharger connector; and pumping a recharging solution from the recharging solution source through the first recharging flow path.

In any embodiment, the method can include connecting a second recharging flow path in a second recharger to the recharging solution source by either: (i) connecting a third recharger connector on the second recharger to a second recharger connector on the first recharger; or (ii) connecting a second recharger connector on the second recharger to a fluid line connecting the recharging solution source to the first recharger connector of the first recharger.

In any embodiment, the method can include the step of pumping a recharging solution from the recharging solution source through the second recharging flow path.

In any embodiment, the step of pumping a recharging solution from the recharging solution source through the second recharging flow path can include pumping the recharging solution from the recharging solution source through the recharger connector on the first recharger, through a second recharger connector on the first recharger, and through a third recharger connector on the second recharger.

In any embodiment, the step of pumping a recharging solution from the recharging solution source through the second recharging flow path can include pumping the recharging solution from the recharging solution source through a fluid line fluidly connected to the first recharger and into the second recharger.

Any of the features disclosed as being part of the third aspect of the invention can be included in the third aspect of the invention, either alone or in combination.

DETAILED DESCRIPTION OF THE INVENTION

Figure 1:
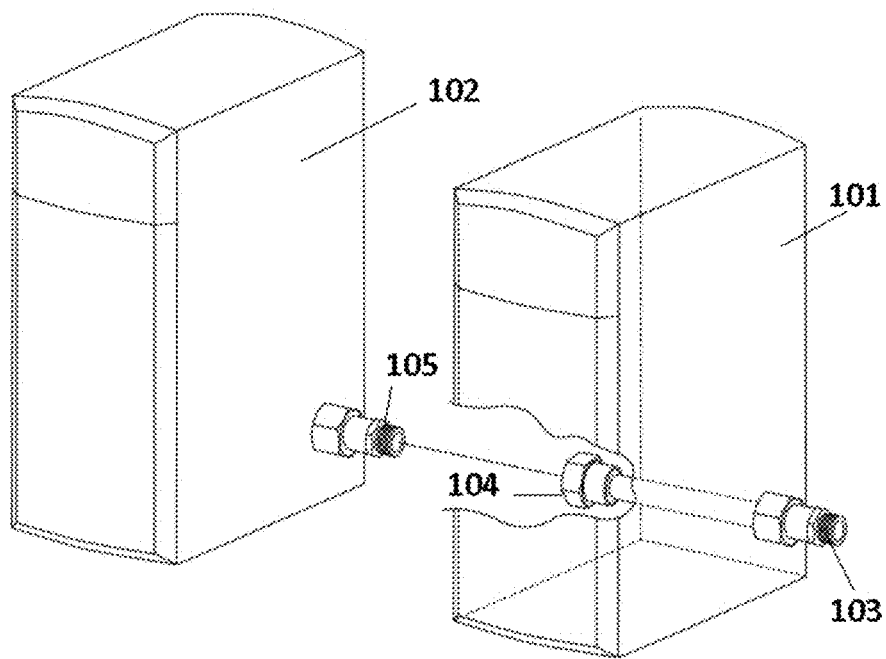
FIG. 1 illustrates two rechargers connected to each other by a twist connect fitting.

Unless defined otherwise, all technical and scientific terms used have the same meaning as commonly understood by one of ordinary skill in the art.

The articles "a" and "an" are used to refer to one or to more than one (i.e., to at least one) of the grammatical object of the article. By way of example, "an element" means one element or more than one element.

An "acid source" is a fluid or concentrate source from which an acidic solution can be obtained.

"Activated carbon" is a carbon material that has been treated to increase the absorptive capacity of the carbon material.

An "activated carbon recharging flow path" is a path through which fluid can travel while recharging activated carbon in a reusable activated carbon sorbent module.

"Alumina," or "aluminum oxide" is a material capable of binding or supporting a catalyst, such as urea.

An "alumina recharging flow path" is a path through which fluid can travel while recharging alumina in a reusable alumina sorbent module.

The term "affixed" refers to a permanent or temporary connection between two components.

A "base source" is a fluid or concentrate source from which a basic solution can be obtained.

A "brine source" is a fluid or concentrate source from which a brine solution can be obtained. As used, a brine solution can refer to any solution comprising acids, bases and/or salts.

A "common reservoir" can be a container for collecting fluid of any type from one or more fluid sources including fluid lines or other reservoirs. The "common reservoir" can for example, store used or waste fluids.

The term "comprising" includes, but is not limited to, whatever follows the word "comprising." Use of the term indicates the listed elements are required or mandatory but that other elements are optional and may be present.

The terms "connecting," "connected," or to "connect" refer to providing for the passage for passing fluid or gas or mixtures thereof, from one point to another point. The two points can be within or between any one or more of compartments, modules, systems, components, and rechargers, all of any type. The connection can optionally be disconnected and then reconnected.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "directly connectable," "directly connected," or "direct connection" refer to a fluid connection between components that does not require additional hose, piping, or flow path beyond the distance required by the direction connection.

A "disinfectant source" is a fluid or concentrate source from which a disinfectant solution can be obtained. The disinfectant solution can be an acidic solution, such as a peracetic acid solution, or any other solution capable of disinfecting reusable sorbent modules.

A "drain" is a fluid line through which fluids may be disposed.

A "drain line" is a fluid line through which used or waste fluid may flow for disposal. The drain line can be connected to a drain, or to a container or reservoir for later disposal of the fluid.

An "end of a fluid connector" refers to a terminus of a fluid connector. The end of the fluid connector can be connected to a second fluid connector, or a component of a system to facilitate the movement of fluid or gas from the fluid connector into the second fluid connector or component.

"Fastenable" or "fastened" refers to the ability to connect two components together such that the two components will resist inadvertent disconnection.

A "fluid" is a liquid substance optionally having a combination of gas and liquid phases in the fluid. Notably, a liquid, as used, can therefore also have a mixture of gas and liquid phases of matter.

The term "fluidly connectable," "fluidly connect," "for fluid connection,", refer to the ability of providing for the passage of fluid or gas or mixtures thereof, from one point to another point. The two points can be within or between any one or more of compartments, modules, systems, components, and rechargers, all of any type. The connection can optionally be disconnected and then reconnected.

A "fluid line" is any conduit through which fluid, gas, or mixtures thereof may flow.

A "module inlet" is a connector through which a fluid, slurry, or aqueous solution can enter a sorbent module.

A "module outlet" is a connector through which a fluid, slurry, or aqueous solution can exit a sorbent module.

The term "outer surface" refers to a surface of a component on the exterior of the component.

The term "pump" refers to any device that causes the movement of fluids, gases, or combinations thereof, by applying suction or pressure.

The terms "pumping," "pumped," or to "pump" refer moving a fluid, gas, or combination thereof, with a pump.

A "receiving compartment" is a space within a recharger into which a sorbent module or other rechargeable dialysis component to be recharged can be positioned.

A "rechargeable dialysis component" is any component or material used in dialysis that can be treated after use to restore the functional capacity of the component.

A "recharger," is an apparatus designed to recharge at least one sorbent material.

A "recharger connector" is a fluid connector through which a fluid or gas can enter or exit a recharger.

A "recharging system" is a system of one or more rechargers to each recharge at least one rechargeable dialysis component.

"Recharging" refers to treating a rechargeable dialysis component to restore the functional capacity of the component to put the component back into a condition for reuse or use in a new dialysis session. In some instances, the total mass, weight and/or amount of "rechargeable" components remain the same. In some instances, the total mass, weight and/or amount of "rechargeable" components change. Without being limited to any one theory of invention, recharging a sorbent material may involve exchanging ions bound to the sorbent material with different ions, which in some instances may increase or decrease the total mass of the system. However, the total amount of the sorbent material will in some instances be unchanged by the recharging process. Upon a rechargeable dialysis component undergoing "recharging," the component can then be said to be "recharged."

A "recharging flow path" is a path through which fluid can travel while recharging sorbent material in a reusable sorbent module or any other rechargeable dialysis component.

A "recharging solution" is a solution having ions for recharging a specific dialysis component.

A "recharging solution source" is a fluid or concentrate source from which a solution used in recharging a dialysis component can be obtained.

A "reusable sorbent module" is a sorbent module containing a sorbent material that can be recharged after use without removing the sorbent material from the sorbent module. After recharging of the sorbent material, the reusable sorbent module can be reused.

A "sealable connector" is a fluid connector that can be opened or closed. Fluid or gas can pass through the connector while opened, but will resist flow when closed, or "sealed."

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

"Sorbent materials" are materials capable of removing specific solutes from solution, such as cations or anions.

A "water source" is a fluid source from which water can be obtained.

"Zirconium oxide," also known as hydrous zirconium oxide, is a sorbent material that removes anions from a fluid, exchanging the removed anions for different anions.

A "zirconium oxide recharging flow path" is a path through which fluid can travel while recharging zirconium oxide in a reusable zirconium oxide sorbent module.

"Zirconium phosphate" is a sorbent material that removes cations from a fluid, exchanging the removed cations for different cations.

A "zirconium phosphate recharging flow path" is a path through which fluid can travel while recharging zirconium phosphate in a reusable zirconium phosphate sorbent module.

Modular Recharging Systems

Plural rechargers can be connected to each other to share infrastructure and resources. The rechargers can be connected to form a recharging system sharing a single source of recharging solutions. In FIG. 1, a first recharger 101 is connected to a second recharger 102. A first recharger connector 103 affixed to an outer surface of the first recharger 101 can be connected to a recharging solution source (not shown in FIG. 1). A recharging solution from the recharging solution source can be pumped into the first recharger 101 through the recharger connector 103. In one non-limiting embodiment, connections to a zirconium oxide and/or a zirconium phosphate recharging flow path can be included (not shown) to deliver the recharging solution to the recharging flow paths. Although zirconium oxide and/or a zirconium phosphate recharging is described, the invention is not limited to those materials and can include any sorbent material or other rechargeable dialysis component used for dialysis known to those skilled in the art. As such, the recharging flow paths can recharge additional types of materials using the plural or ganged recharger system of the present invention. The ganged systems and methods can also recharge one or more sorbent cartridge wherein any one or more of the sorbent cartridges can be single-use, multi-use, and combinations thereof.

In FIG. 1, the recharging solution can exit the first recharger 101 through a second recharger connector 104 affixed to an outer surface of the recharger, and enter the second recharger 102 through a third recharger connector 105 on the second recharger. The second recharger connector 104 of the first recharger 101 can be directly connected to the third recharger connector 105 of the second recharger 102 to facilitate the movement of the recharging solution through the first recharger 101 to the second recharger 102. The second recharger 102 can also include a fourth recharger connector (not shown) for connection to a recharger connector of a third recharger. Individual rechargers of the ganged recharger system can recharge one or more different types of sorbent materials contained in one or more multi-use sorbent cartridges, or any other rechargeable dialysis component. For example, a first recharger can recharge zirconium oxide in a multi-use cartridge, a second recharger of the system can recharge zirconium phosphate in a multi-use sorbent cartridge, and a third recharger of the system can recharge a second layer of zirconium oxide in a multi-use sorbent cartridge. Any combination of sorbent materials in multi-use sorbent cartridges or other rechargeable dialysis components recharged by any number of rechargers are contemplated by the invention. In particular, the rechargers can be connected together as needed to allow any number of rechargers to share a single recharging solution source, including 2, 3, 4, 5, 6, or more rechargers. Although the first recharger connector 103, serving as an inlet, is illustrated as a male portion of the connector and the second recharger connector 104, serving as an outlet, is illustrated as the female portion of the connector, one of skill in the art will understand that the recharger inlet can have the female portion and the recharger outlet the male portion of the connectors. Further, any arrangement of male and female connectors between the rechargers is contemplated. For example, a first recharger can two male connectors as the inlet and outlet, or can have two female connectors as the inlet and outlet.

FIG. 1 illustrates the recharger connector of a first recharger directly connected to a recharger connector of the second recharger. Alternatively, each of the recharger connectors can connect to a separate fluid line connecting the two rechargers. The recharger connector 104 can connect to a first end of a fluid connector, while the recharger connector 105 of the second recharger can connect to the second end of the fluid connector. Using a separate fluid line may enable easier connection between the two rechargers.

As described, recharging zirconium phosphate in a rechargeable sorbent module can require a disinfectant solution, a brine solution, and water. An acid solution can optionally be included for recharging of zirconium phosphate. Recharging zirconium oxide in a rechargeable sorbent module can require a disinfectant solution, a base solution, and water. The fluid line formed by connecting recharger connector 104 of the first recharger 101 to recharger connector 105 on the second recharger 103 can be connected to any recharging solution source used in recharging zirconium phosphate or zirconium oxide. Although a single fluid line is illustrated in FIG. 1, additional fluid lines can be included to connect the rechargers to each recharging solution source. Any number of recharger connectors can be provided on the rechargers, including 1, 2, 3, 4, 5, or more recharger connectors on each recharger.

The rechargers can be used for concurrent or independent recharging of zirconium phosphate and zirconium oxide in rechargeable sorbent modules. Certain recharging solutions, such as water and disinfectant, can be used in both the zirconium phosphate and zirconium oxide recharging processes. Separate flow paths for recharging zirconium oxide and zirconium phosphate can be provided, with the recharging solutions connected to each flow path as required. For example, a water source can be connected to both the zirconium phosphate and zirconium oxide recharging flow paths, while a brine source and/or an acid source can be connected to only the zirconium phosphate recharging flow path. For recharging solutions used in both flow paths, a single recharger connector can be provided, with the recharging solution connected through the inlet to both flow paths. Alternatively, each recharger can have multiple recharger connectors for each recharging solution with separate inlets for each of the zirconium phosphate and zirconium oxide recharging flow paths.

The rechargers can be configured for recharging both zirconium phosphate and zirconium oxide in sorbent modules, or the recharger can be configured for recharging solely zirconium oxide and zirconium phosphate. Each recharger can include one or more receiving compartments for receiving and recharging any combination of zirconium phosphate or zirconium oxide sorbent modules. Any number of receiving compartments can be included in each recharger, including 1, 2, 3, 4, 5, 6, or more receiving compartments for any combination of sorbent modules. In addition to zirconium oxide and zirconium phosphate sorbent modules, sorbent modules containing other sorbent materials, as well as any other rechargeable dialysis components, can be recharged with the systems illustrated. A recharger can include an activated carbon recharging flow path having an activated carbon module inlet and an activated carbon module outlet for connection to an activated carbon sorbent module. Activated carbon can be recharged with hot water, and/or base, and so a water source and/or base source can be connected to the activated carbon recharging flow path. A recharger can also include an alumina recharging flow path having an alumina module inlet and an alumina module outlet for connection to an alumina sorbent module. Alumina can be recharged with a base solution, and so a base source can be connected to the alumina recharging flow path in one or more rechargers. Any combination of one or more sorbent modules can be recharged using the described systems.

Further a single sorbent module can include more than one sorbent material. For example, a sorbent module may contain both activated carbon and alumina. Both materials in the sorbent module can be recharged with water and base.

Figure 2:
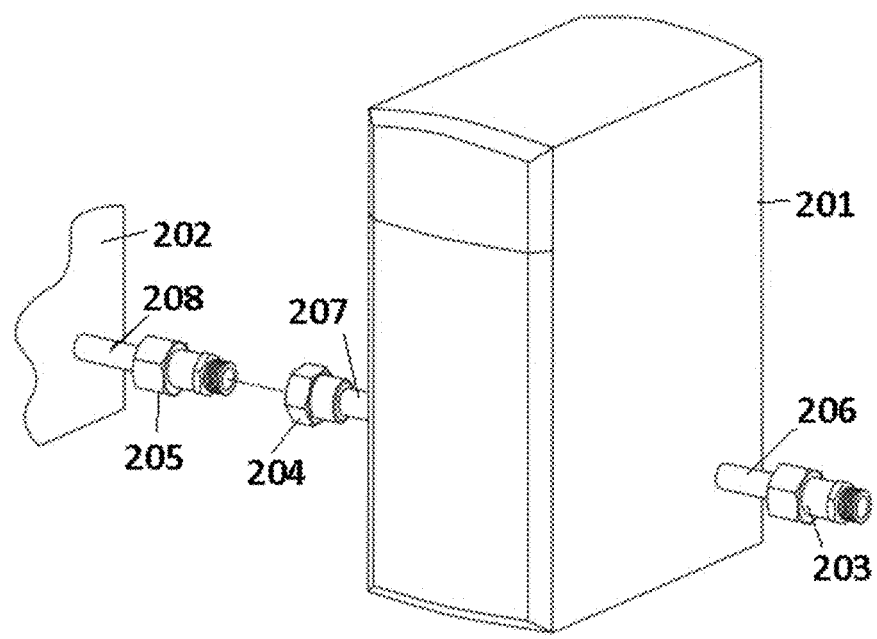
FIG. 2 illustrates a recharger and fittings.

As illustrated in FIG. 2, the recharger connectors can be positioned on a fluid line or tube connected to the rechargers. Recharger 201 can have a first recharger connector 203 connected to the recharger 201 by fluid line 206. The recharger 201 can have a second recharger connector 204 connected to the recharger 201 by fluid line 207. A recharging solution can enter the recharger 201 through recharger connector 203 where the recharging solution can be directed to either or both of a zirconium oxide recharging flow path or a zirconium phosphate recharging flow path. The recharging solution can exit the recharger 201 through recharger connector 204. The recharger connector 204 can connect to a recharger connector 205 of a second recharger 202 through fluid line 208.

Figure 3:
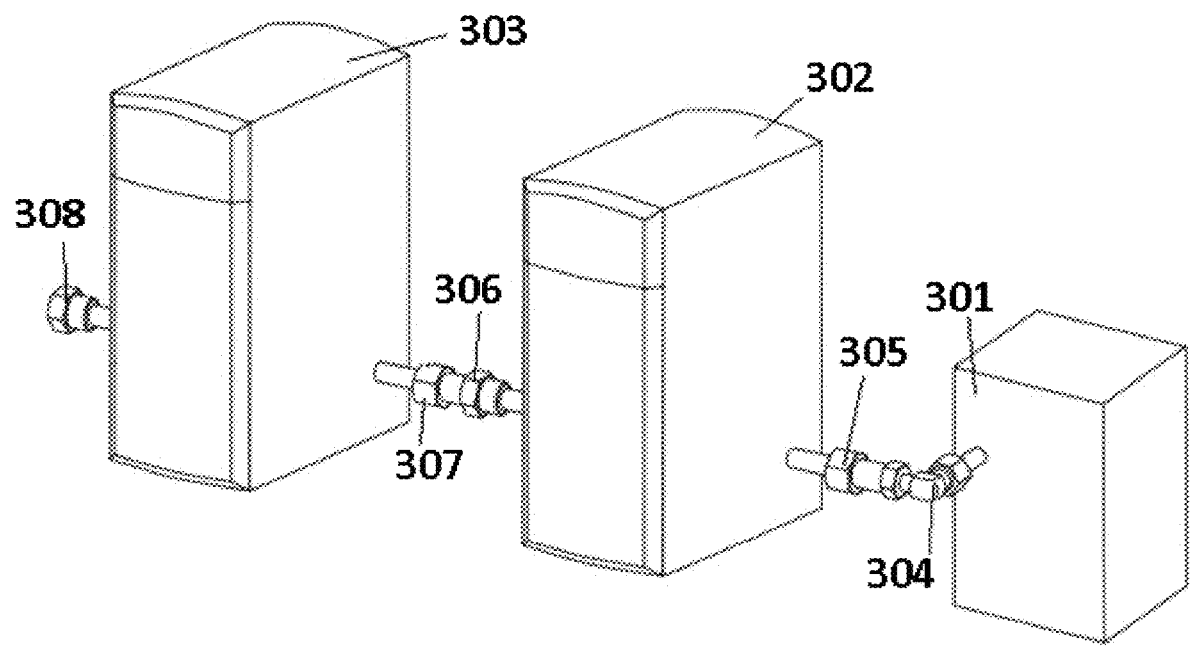
FIG. 3 illustrates two rechargers connected to each other and to a recharging solution source.

FIG. 3 illustrates multiple rechargers connected together and to a recharging solution source. The recharging solution source 301 can be connected to a first recharger 302 through recharging solution source outlet 304 and recharger connector 305. The recharging solution can be directed to either or both a zirconium phosphate recharging flow path and a zirconium oxide recharging flow path in the first recharger 302. The recharging solution can exit the first recharger 302 through recharger connector 306, which can be fluidly connected to a recharger connector 307 of a second recharger 303. The recharging solution can be directed to either or both of a zirconium phosphate recharging flow path or a zirconium oxide recharging flow path in the second recharger 303. A third recharger (not shown) can be connected to the recharger connector 308 of the second recharger 303. Any number of rechargers can be connected together as illustrated in FIG. 3 to allow recharging of any number of sorbent modules.

Figure 4:
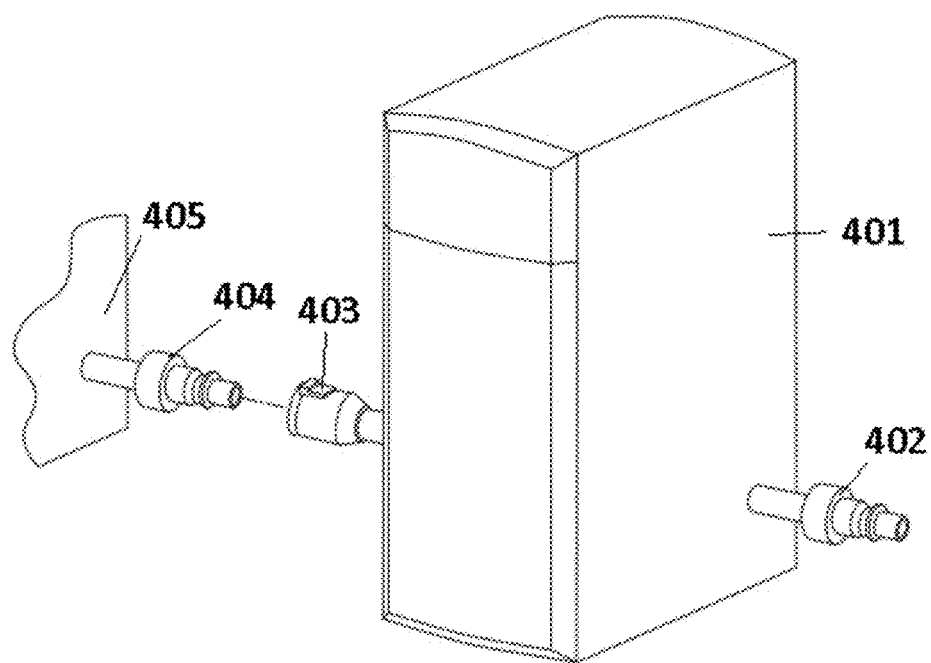
FIG. 4 illustrates recharger and snap connect fittings.

FIGS. 1-3 illustrate rechargers with twist-connect fittings on the recharger inlets and recharger outlets. The recharger connectors are fastenable, allowing connection between two rechargers while resisting inadvertent detachment. The connectors connect together by twisting the male portion of the connector with respect to the female portion of the connector. Once connected, the threaded portion will prevent the rechargers from disconnecting unless the male and female portions of the connector are twisted in the opposite direction. However, any type of connector can be used. FIG. 4 illustrates rechargers with snap-connect fittings. A first recharger 401 has a first recharger connector 402 affixed to an outer surface of the recharger 401 and fluidly connected to a recharging solution source. The first recharger 401 also has a second recharger connector 403 affixed to an outer surface of the recharger 401 that can connect to a third recharger connector 404 of a second recharger 405. The recharger connector 403 of the first recharger 401 and the recharger inlet 404 of the second recharger 405 are fastenable, and can snap together to form a seal without the need to twist the connectors. The male portion on the recharger connector 404 need only be inserted into the female portion of the recharger connector 403 to connect the rechargers. A locking mechanism (not shown) can be included to ensure that the connectors do not disengage accidently during use.

Figure 5:
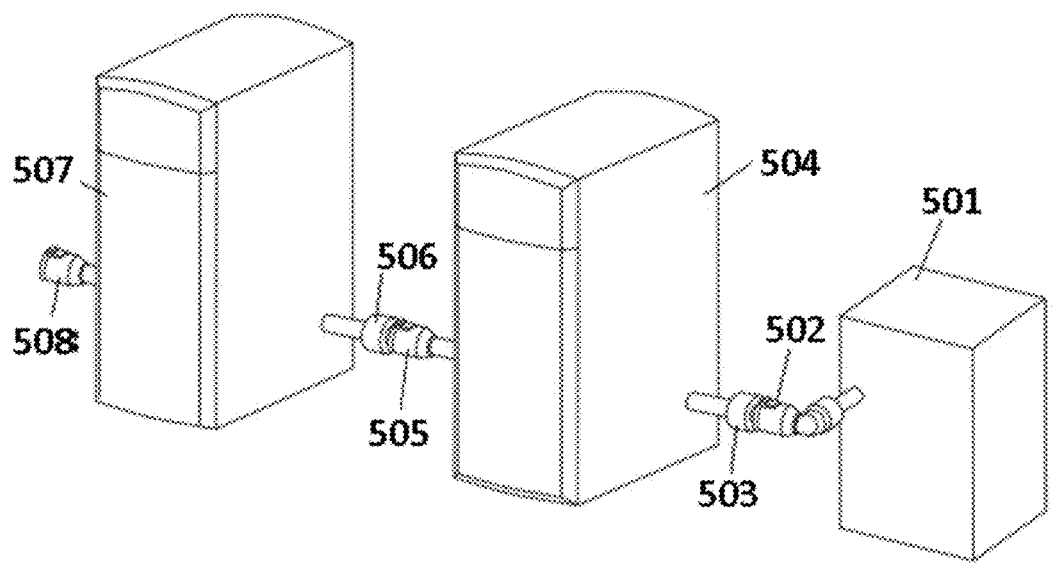
FIG. 5 illustrates multiple rechargers connected together.

FIG. 5 illustrates multiple rechargers connected to a recharging solution source by snap-connect fittings. A recharging solution source can be pumped from the recharging solution source 501 through connector 502, fluidly connected to a first recharger connector 503 of a first recharger 504. The recharging solution can be directed to either or both of a zirconium phosphate recharging flow path and a zirconium oxide recharging flow path in the first recharger 504. The recharging solution can exit the first recharger 504 through a second recharger connector 505, which can be fluidly connected to a third recharger connector 506 of a second recharger 507. The recharging solution can be directed to either or both of a zirconium phosphate recharging flow path or a zirconium oxide recharging flow path in the second recharger 507. A third recharger (not shown) can be connected to the recharger connector 508 of the second recharger 507. Any number of rechargers can be connected together as illustrated in FIG. 5 to allow recharging of any number of sorbent modules.

Figure 6:
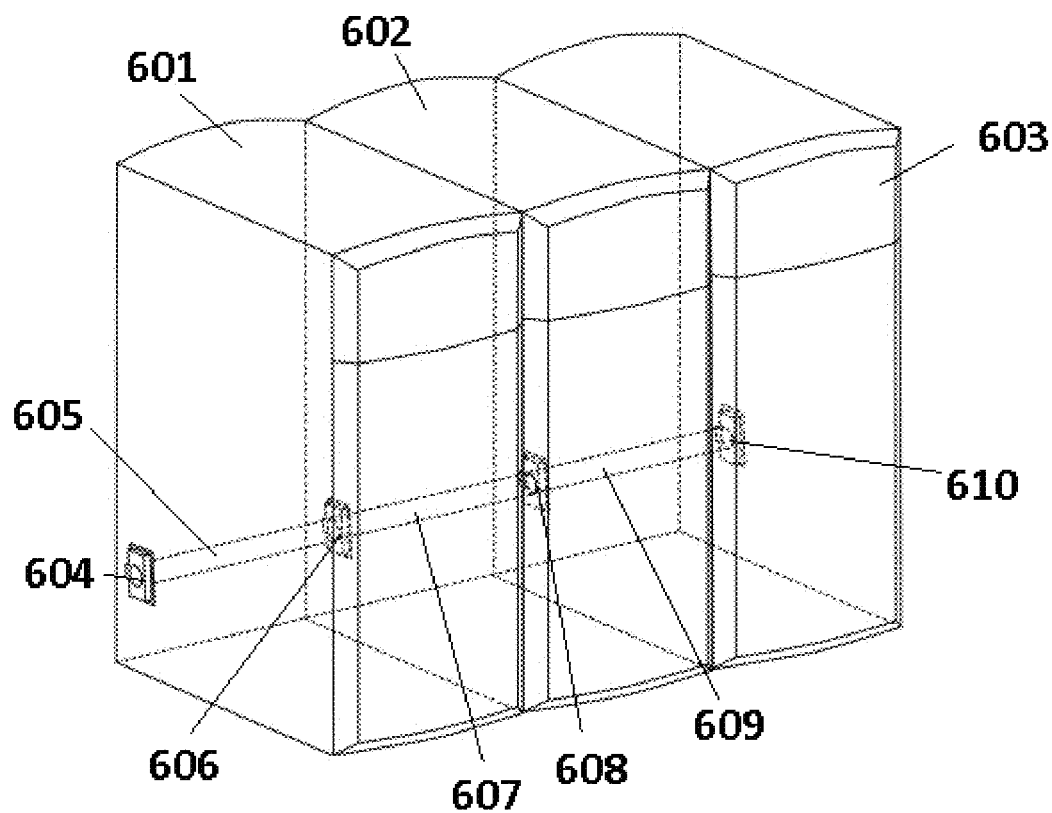
FIG. 6 illustrates multiple rechargers connected together and to a single fluid line.

FIG. 6 illustrates rechargers connected together in direct contact. A recharging solution can be pumped from a recharging solution source (not shown) into a recharger connector affixed to an outer surface of first recharger 601. The recharging solution can be directed to a zirconium phosphate and/or zirconium oxide recharging flow path within the first recharger 601. The recharging solution can flow through the first recharger 601 through fluid line 605. A second recharger connector affixed to an outer surface of the first recharger 601 can directly connect to a third recharger connector affixed to an outer surface of a second recharger 602 at junction 606. The recharging solution can pass directly from fluid line 605 in the first recharger 601 into fluid line 607 in second recharger 602. In the second recharger 602, the recharging solution can be directed to either or both of a zirconium phosphate and zirconium oxide recharging flow path, as described. The recharging solution can pass through fluid line 607 and into a fluid line 609 of the third recharger 603 through a junction 608 formed by connecting the recharger connector of the second recharger 602 to a recharger connector of the third recharger 603. The recharging solution can be directed to either or both of a zirconium phosphate and zirconium oxide recharging flow path in the third recharger 603. A fourth recharger (not shown) can be directly connected to the recharger connector 610 of the third recharger 603 as needed. Any number of rechargers can be connected in direct contact as illustrated in FIG. 6 for recharging any number of sorbent modules.

Figure 7:
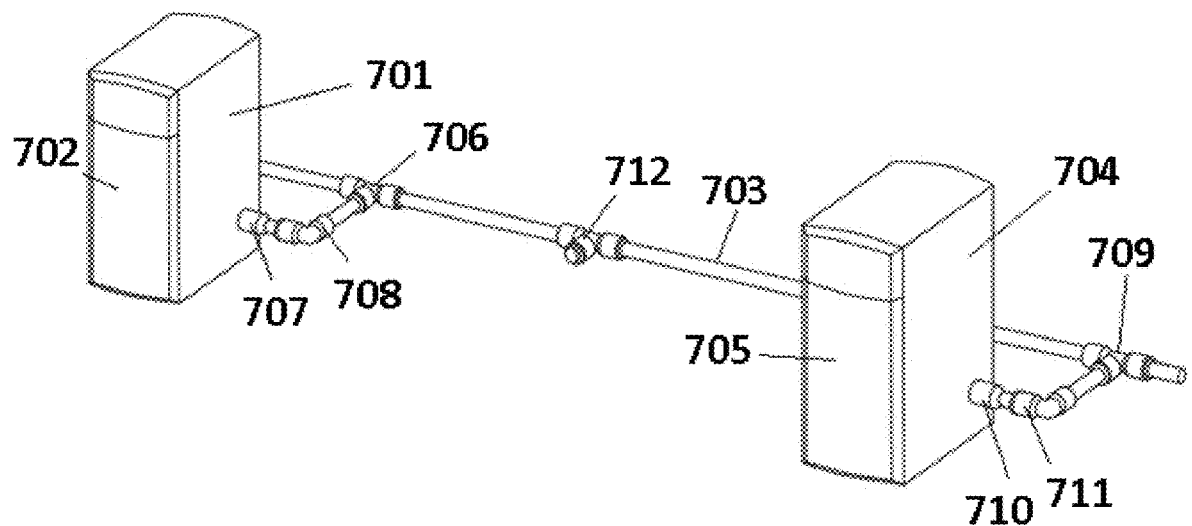
FIG. 7 illustrates a fluid line having three connections with two connected to rechargers.

FIG. 7 illustrates a non-limiting embodiment of a modular recharging system including one or more rechargers connected to a single source for recharging solutions through a single fluid line. A fluid line 703 can be connected to a recharging solution source. A first recharger 701 can be connected to the fluid line 703 from a recharger connector 706 on the fluid line 703, through a recharger connector 708, and into a recharger inlet 707 affixed to an outer surface of the recharger 701. Fluid from the fluid line 703 can be pumped into the recharger as needed for recharging the sorbent materials. A second recharger 704 can be connected to the fluid line 703 from a recharger connector 709, through a fluid connector 711 and into the second recharger inlet 710. The first recharger 701 and second recharger 704 are each connected to a single fluid line 703 for each recharging fluid, allowing a single recharging solution source to be used for each type of recharging solution. Door 702 on the first recharger 701 and door 705 on the second recharger 704 control access to the interior of the recharger during use. The rechargeable sorbent modules can be placed in the recharger and recharged as described.

The fluid line 703 can accommodate any number of rechargers. As illustrated in FIG. 7, an additional recharger connector 712 can be included on the fluid line 703 to connect a third recharger. Additional rechargers can be connected to the fluid line 703 as necessary. Any number of recharger connectors can be included on the single fluid line 703, including 3, 4, 5, 6, 7, 8 or more recharger connectors to accommodate any number of rechargers. Any number of rechargers can be connected to the fluid line 703 and used to recharge sorbent materials, either concurrently or independently.

The recharger connectors can be sealable connectors to allow use of the single fluid line 703 when one or more recharger connectors are not in use. A sealable connector can be opened when connected to a recharger, or closed when not connected to a recharger to prevent the recharging solution from spilling out of the fluid line 703. Additionally, a sealable connector can be sealed when connected to a recharger while not in use and opened when the recharging process begins.

Figure 8:
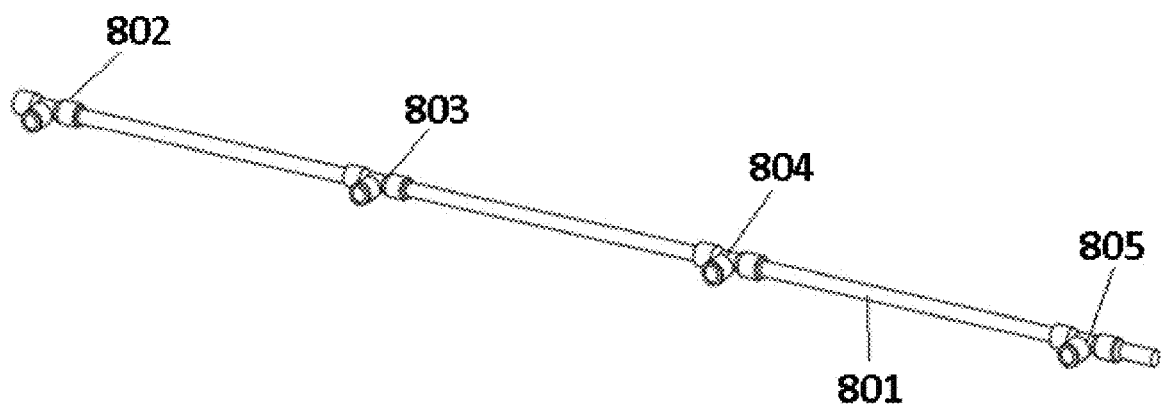
FIG. 8 illustrates a fluid line connectable to multiple rechargers.

FIG. 8 illustrates a fluid line 801 with multiple recharger connectors 802, 803, 804, and 805 for connection to multiple rechargers. As described, any number of recharger connectors can be included on the fluid line 801. The recharger connectors 802-805 and fluid line 801 can be formed from any material known in the art, including steel, cast iron, bronze, carbon steel, plastic, polymer, or any other material known in the art compatible with the recharging solutions.

Figure 9:
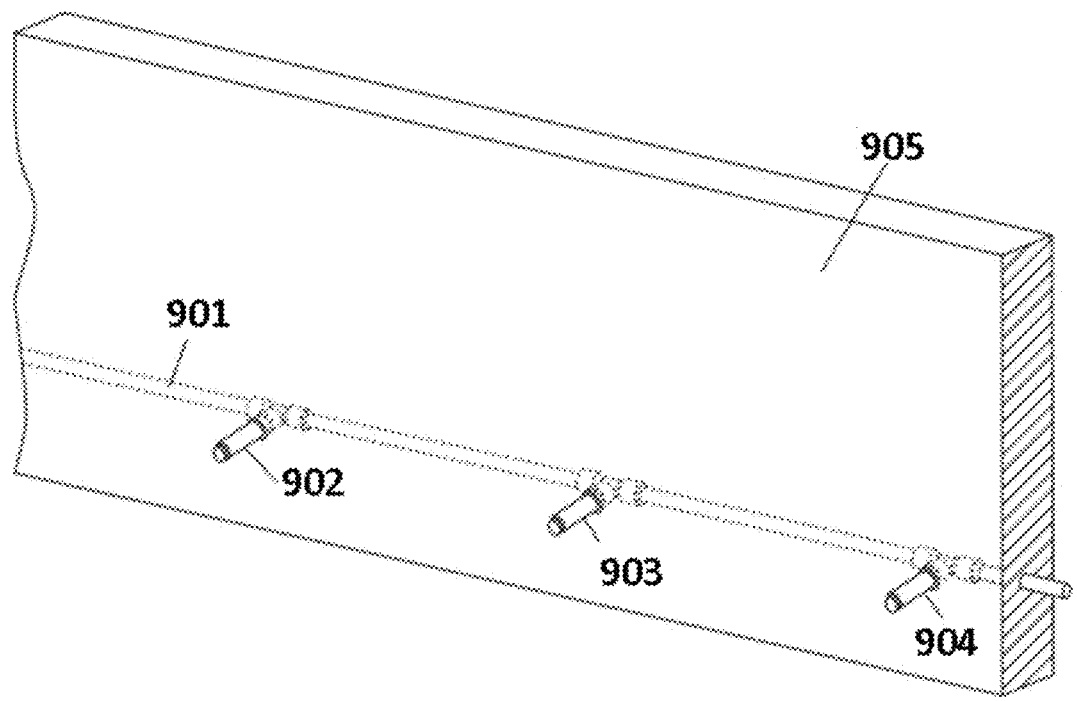
FIG. 9 illustrates a fluid line connectable to multiple rechargers embedded in a wall.
Figure 10:
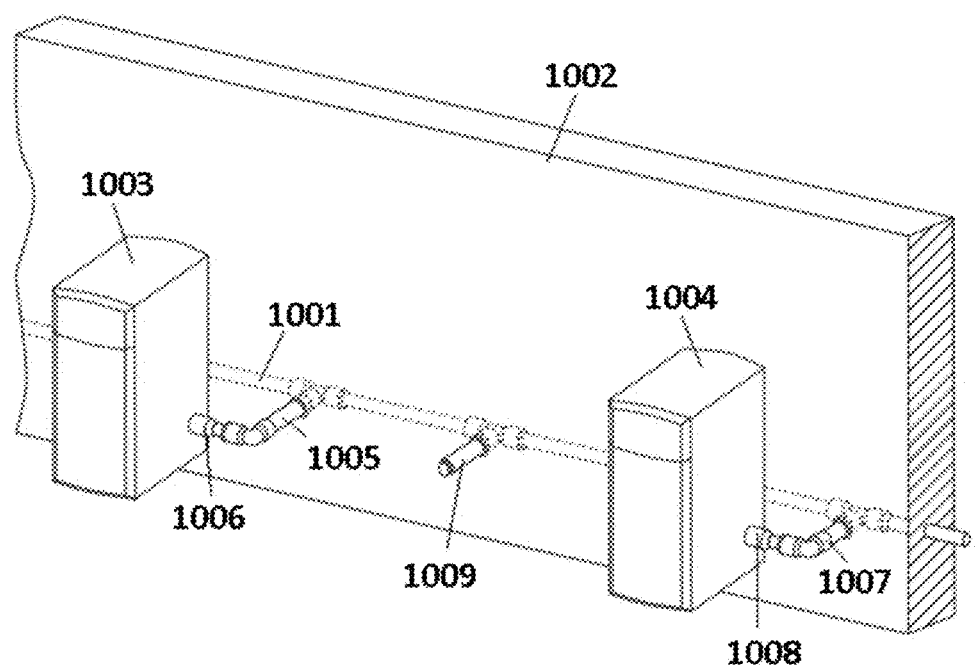
FIG. 10 illustrates a fluid line embedded in a wall and connected to rechargers.

As illustrated in FIG. 9, the fluid line 901 may be embedded in a wall 905 to save space. The fluid line 901 can be connected to a recharging solution source (not shown), and pass through the wall 905. Recharger connectors 902, 303, and 904 can extend outwardly from the wall 905 for easy connection to rechargers. FIG. 10, illustrates a fluid line 1001 embedded in a wall 1002 and connected to rechargers 1003 and 1004. Fluid from fluid line 1001 can enter recharger 1003 through recharger connector 1005 connected to recharger inlet 1006. Fluid from fluid line 1001 can enter recharger 1004 through recharger connector 1007 connected to recharger inlet 1008. An additional recharger connector 1009 is shown for connection to a third recharger as needed.

Figure 11:
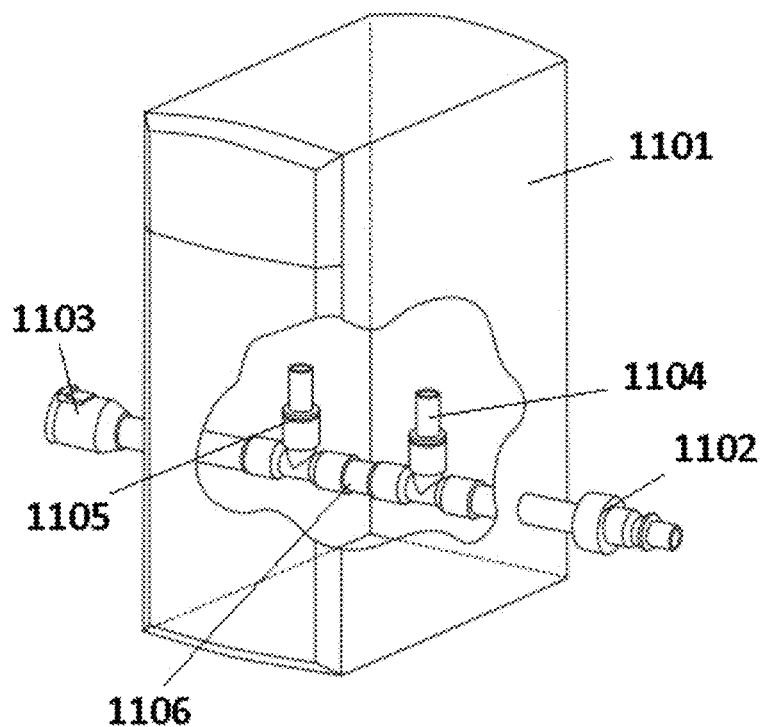
FIG. 11 illustrates a fluid line configured to convey a recharging solution to a zirconium phosphate and a zirconium oxide recharging flow path within a recharger.

FIG. 11 illustrates an interior of a recharger configured to recharge zirconium oxide and zirconium phosphate. A recharging solution can be pumped into the recharger 1101 through recharger inlet 1102 affixed to an outer surface of the recharger 1101. The recharging solution can pass through the recharger 1101 through fluid line 1106. A connector 1104 can fluidly connect the fluid line 1106 to a zirconium oxide recharging flow path (not shown). A second connector 1105 can fluidly connect the fluid line 1106 to a zirconium phosphate recharging flow path (not shown). The connectors 1104 and 1105 allow the recharging solution to be directed to either or both of the zirconium oxide and zirconium phosphate recharging flow paths. The recharging solution can exit the recharger 1101 through recharger outlet 1103 to enter a second recharger.

As illustrated in FIG. 11, a single recharging solution can be directed to both of a zirconium phosphate and zirconium oxide recharging flow path. As described, the rechargers can be used to recharge solely zirconium oxide or solely zirconium phosphate. Where the recharger is only used to recharge a single sorbent material, only a single internal connector is needed. Further, certain recharging solutions are only used in recharging either zirconium oxide or zirconium phosphate. The fluid lines conveying a recharging solution used in only a single flow path can also have only a single connector.

Figure 12:
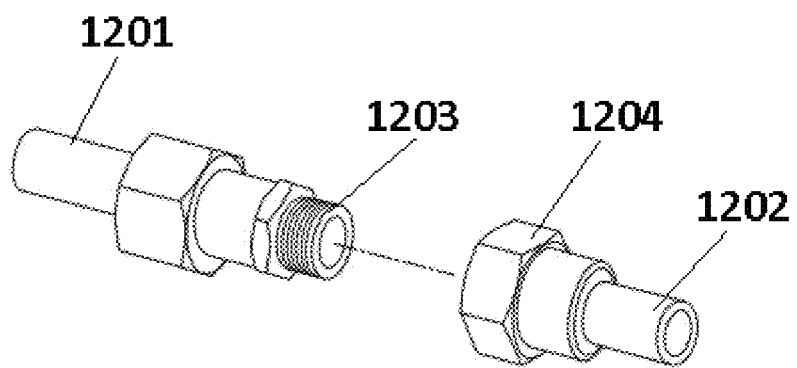
FIG. 12 is a close-up view of a twist connect fitting.

FIG. 12 illustrates a close-up of the fastenable connection between rechargers using a twist-connect fitting as illustrated in FIGS. 1-3. The recharger outlet 1202 of a first recharger can include a female portion 1204 of a fitting. The recharger inlet 1201 of a second recharger can include the male portion 1203 of the fitting. To connect the rechargers together, male portion 1203 is inserted into female portion 1204, and the fitting twisted to connect the inlet and outlet. The threaded area on the male portion 1203 and a grooved area (not shown) on the female portion 1204 fit together to ensure the rechargers do not inadvertently disconnect.

Figure 13:
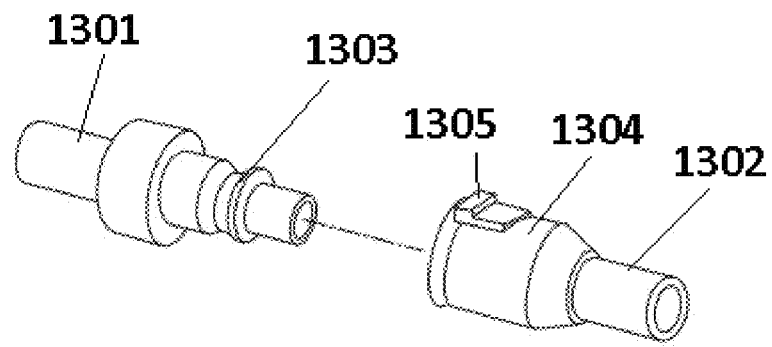
FIG. 13 is a close-up view of a snap connect fitting.

FIG. 13 illustrates a close-up of the fastenable connection between rechargers using a snap-connect fitting as illustrated in FIGS. 4-5. The recharger outlet 1302 of a first recharger can include a female portion 1304 of a fitting. The recharger inlet 1301 of a second recharger can include the male portion 1303 of the fitting. To connect the rechargers together, male portion 1303 is inserted into female portion 1304. Once engaged, latch 1305 snaps over the male portion 1303 to hold the fittings together. The latch 1305 can be disengaged to allow disconnection of the fittings and separation of the rechargers.

Figure 14:
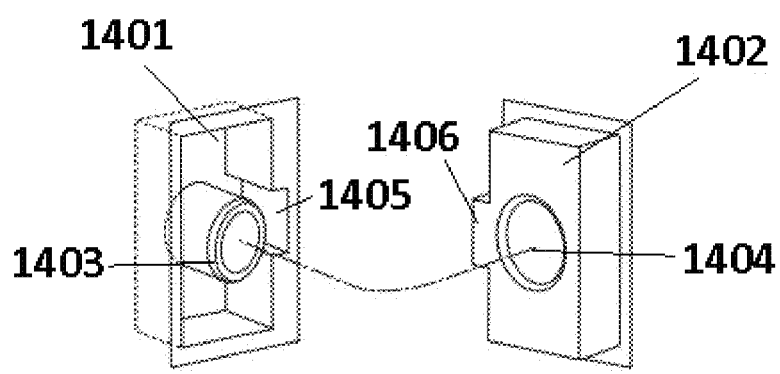
FIG. 14 is a close view of a direct connection between rechargers.

FIG. 14 illustrates a close-up of the fastenable connection between rechargers using a direct connection as illustrated in FIG. 6. The recharger outlet 1402 of a first recharger can include a female portion 1404 of a fitting. The recharger inlet 1401 of a second recharger can include the male portion 1403 of the fitting. When the rechargers are placed directly together, the male portion 1403 fits within the female portion 1404 of an adjacent recharger. Notch 1405 of recharger inlet 1401 and flange 1406 of recharger outlet 1402 ensure a proper fit between the rechargers. Notch 1405 and flange 1406 can be sized and shaped to ensure the rechargers connect with a proper alignment. Additional latches, locks, threads, or other mechanisms can be included to ensure a sealed connection between the two rechargers.

Any of the fastenable connectors described can have a locking mechanism to prevent inadvertent detachment of the connectors during use and prevent leaks. The locking mechanisms can include latches or threaded fittings that mate together creating a seal. Fasteners can be fitted around the connectors after connection to further enhance stability of the connections. O-rings made of rubber, plastic, or an elastomeric material can be included to in the connectors to prevent leakage. The inner or outer portions of the connectors can be made from a deformable elastomeric material which adapts to the shape of the opposing connector, creating a fluid-tight seal. Any other type of connector, locking mechanism, or sealing mechanism is within the scope of the invention.

Figure 15:
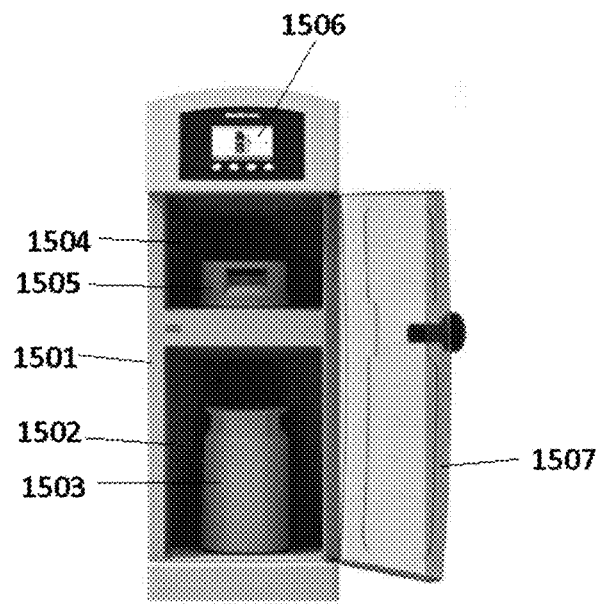
FIG. 15 illustrates a recharger for recharging zirconium phosphate and zirconium oxide.

FIG. 15 illustrates a non-limiting embodiment of a recharger 1501 configured for recharging zirconium phosphate and zirconium oxide modules. The recharger 1501 can have a zirconium phosphate receiving compartment 1502 configured to hold a zirconium phosphate sorbent module 1503. The recharger 1501 can also have a zirconium oxide receiving compartment 1504 configured to hold a zirconium oxide sorbent module 1505. Fluid connectors (not shown in FIG. 6) can provide fluid connection to the recharging solution sources described, either directly to a fluid line connectable to multiple rechargers, or through separate rechargers to the recharging solution sources. As described, any one or more fluid sources can be housed within the recharger 1501 or outside of the recharger 1501 with fluid connectors connecting the fluid sources to the recharging flow paths. The recharger 1501 can have a door 1507 which can prevent access to the reusable modules during operation. The recharger 1501 can also have a user interface 1506. The user interface 1506 can start or control the recharging process by the user. Further, the user interface 1506 can provide the status of the recharging process to the user such as the times to completion for each recharging step. User interface 1506 can also provide alert messages if any problems are detected during recharging, such as leaks, occlusions, pump failures, or mismatched chemicals. Rechargers with any number of receiving compartments for recharging any number or combination of zirconium oxide and/or zirconium phosphate sorbent modules can be constructed. For example, a recharger with two zirconium phosphate receiving compartments and two zirconium oxide receiving compartments can be similarly constructed. The rechargers can have 1, 2, 3, 4, 5, 6, or more receiving compartments, each capable of receiving zirconium oxide or zirconium phosphate sorbent modules. One or more recharger connectors can be provided for each of the recharging solutions to allow connection to a common fluid line used by multiple rechargers, or a direct connection to another recharger to facilitate sharing of infrastructure and resources.

Figure 16:
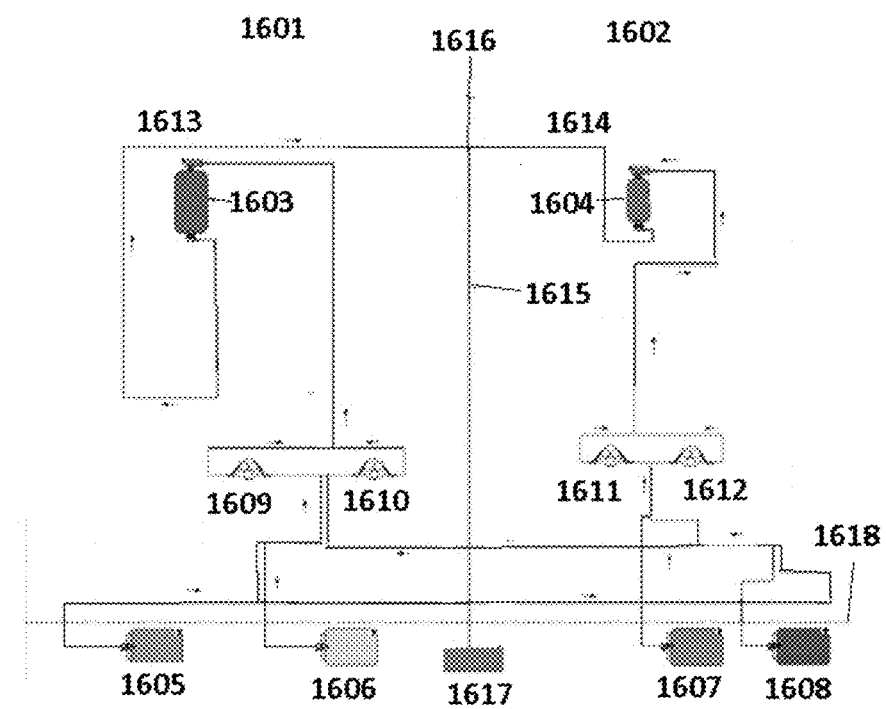
FIG. 16 is a generalized view of a zirconium phosphate and zirconium oxide recharging flow path.

FIG. 16 illustrates a generalized view of the zirconium phosphate and zirconium oxide recharging flow paths. The recharging flow path can be divided into a zirconium phosphate recharging flow path 1601 containing the zirconium phosphate module 1603 and a zirconium oxide recharging flow path 1602 containing zirconium oxide module 1604. Although a dual cartridge recharging system is shown, single, two, three, or more multiple cartridge recharging systems are envisioned. As described, the recharger systems can be linked together to share resources for recharging the sorbent cartridge and can be adapted for large scale use. Similarly, the linked rechargers can be scaled down as demand for recharging decreases. The modular recharging set-up having more or less rechargers based on demand can be advantageously used where required.

The zirconium phosphate recharging flow path 1601 has a water source 1605, a brine source 1606, a disinfectant source 1607, and a base source 1608. An optional acid source (not shown) can be included for recharging zirconium phosphate. The recharging solution sources can be housed outside of the recharger housing, illustrated as dotted line 1618. Although shown as directly connected to the recharging flow paths in FIG. 16, the recharging solution sources can be connected through additional rechargers to the zirconium phosphate recharging slow path 1601 and the zirconium oxide recharging flow path 1602, as described. The brine source 1606, disinfectant source 1607, and/or base source 1608 can be a column containing a dry bed of the brine, disinfectant, and/or base components. Alternatively, a powdered source of the brine, disinfectant, and/or base components can be used. The dry bed or powdered source can be dissolved with an aqueous solution. A static mixer (not shown) can mix the single line coming through the column prior to entering the zirconium phosphate module 1603 or zirconium oxide module 1604. Recharging the zirconium phosphate in a zirconium phosphate module 1603 requires water, brine or acid, and disinfectant. The water source 1605, the brine source 1606 and/or acid source (not shown), and the disinfectant source 1607 are fluidly connected to the zirconium phosphate recharging flow path 1601. Similarly, recharging zirconium oxide module 1604 in zirconium oxide recharging flow path 1602 requires water, base, and disinfectant. The water source 1605, the disinfectant source 1607, and the base source 1608 can be fluidly connected to the zirconium oxide recharging flow path 1602. The zirconium phosphate recharging flow path 1601 and zirconium oxide recharging flow path 1602 can be operated simultaneously or independently. Disinfectant source 1607 can contain any type of disinfectant compatible with zirconium phosphate and zirconium oxide capable of disinfecting the reusable sorbent modules. In any embodiment, the disinfectant source 1607 can contain peracetic acid. In any embodiment, the peracetic acid can be a solution of between 0.5% and 2% peracetic acid in water. Alternatively, the disinfectant source 1607 can contain any disinfectant compatible with zirconium phosphate and zirconium oxide, including bleach or citric acid. The brine source 1606 can have an acid, a base, and a sodium salt.

During zirconium phosphate recharging, potassium, calcium, magnesium, and ammonium ions bound to the zirconium phosphate must be replaced by hydrogen and sodium ions. The final ratio of hydrogen to sodium ions on the recharged zirconium phosphate can be determined by the pH, buffer capacity, and sodium concentration of the brine solution or acid solution used in the recharging process. The brine source 1606 can be a mixture of sodium chloride, sodium acetate, and acetic acid. In one non-limiting brine solution, the sodium chloride concentration can be between 2.5 M and 4.9 M, the sodium acetate concentration can be between 0.3 M and 1.1 M, and acetic acid concentration can be between 0.2 M and 0.8 M. The water source 1605 can contain any type of water, including deionized water. To recharge the zirconium phosphate in the zirconium phosphate module 1603, the disinfectant from disinfectant source 1607 can flow to the zirconium phosphate module 1603 to disinfect the zirconium phosphate module 1603. Zirconium phosphate pumps 1609 and 1610 provide a driving force to pump the fluid through the zirconium phosphate recharging flow path 1601. Use of two or more separate pumps can reduce wear on the pumps. Correspondingly, smaller pumps can be used. The two or more pumps can provide in-line mixing and intermittent pumping so at any given time, a single pump can pump fluid through the zirconium phosphate recharging flow path 1601. The two pumps can be used simultaneously or independently. The two or more pumps can provide fluid line mixing of one or more separate fluid streams when used simultaneously. The two or more pumps can operate asynchronously but used concurrently. For example, a first pump can operate for a time and a second pump remain off, then the first pump shut off with the second pump turning on. Multiple pumps at various timed pumping stages are envisioned as described. One of skill in the art will understand that a single zirconium phosphate pump can also accomplish the described pump functions.

During filling, fluid inside zirconium phosphate module 1603 can be forced through the zirconium phosphate module outlet and into zirconium phosphate module effluent line 1613. The disinfectant can be sequestered in the zirconium phosphate module 1603 to ensure disinfection. A heater (not shown) can heat the disinfectant because disinfection can become more efficient at elevated temperatures. The heater can be positioned inside of the recharger in the recharging flow path, or alternatively the heater can heat the fluid in the fluid sources, allowing a single heater for any number of rechargers. After disinfection, zirconium phosphate module 1603 can be rinsed using water from water source 1605. Zirconium phosphate pumps 1609 and 1610 can pump water through the zirconium phosphate module 1603 through the zirconium phosphate module inlet, out the zirconium phosphate module outlet and into zirconium phosphate module effluent line 1613. Water can be pumped through the zirconium phosphate module 1603 until all of the disinfectant is removed.

Fluid from brine source 1606 and/or an acid source can be pumped through the zirconium phosphate module 1603 to load the zirconium phosphate module 1603 with the proper ratio of sodium and hydrogen ions. Zirconium phosphate pumps 1609 and 1610 can pump fluid from brine source

1606 through zirconium phosphate module 1603 and into zirconium phosphate module effluent line 1613. A heater, either inside or outside of the recharger, can heat the brine because recharging can become more efficient at elevated temperatures. A heat exchanger (not shown) can be included in the zirconium phosphate recharging flow path 1601 to reduce the burden on the heater by using the increased temperature of the zirconium phosphate effluent to partially heat the fluid in the zirconium phosphate inlet lines. The zirconium phosphate module 1603 can be rinsed again by pumping water through the zirconium phosphate module 1603. A static mixer (not shown) can be positioned upstream of the zirconium phosphate module 1603 and mix the solutions prior to entering the zirconium phosphate module 1603.

To recharge the zirconium oxide module 1604, disinfectant from disinfectant source 1607 can be first pumped to the zirconium oxide module 1604 to disinfect the zirconium oxide module 1604. Zirconium oxide pumps 1611 and 1612 can pump fluid through the zirconium oxide recharging flow path 1602. As described, a single zirconium oxide pump can be an alternative to the dual pump system in FIG. 16. Also, two or more zirconium oxide pump are contemplated. The two or more zirconium oxide pumps can provide fluid line mixing of one or more separate fluid streams when used simultaneously. The two or more zirconium oxide pumps can be asynchronous but used concurrently. For example, a first pump can operate for a time and a second pump remain off, then the first pump shut off with the second pump turning on. Multiple pumps at various timed pumping stages are envisioned as described. Zirconium oxide pumps 1611 and 1612 pump fluid from disinfectant source 1607 to the zirconium oxide module 1604 through a zirconium oxide module inlet. During filling, fluid inside zirconium oxide module 1604 can flow through a zirconium oxide module outlet and into zirconium oxide module effluent line 1614. The disinfectant can be sequestered in zirconium oxide module 1604 to ensure disinfection. The zirconium oxide module 1604 can then be flushed with water from water source 1605 after disinfection is completed. Zirconium oxide pumps 1611 and 1612 can pump water from water source 1605 to zirconium oxide module 1604 through the zirconium oxide module inlet and out the zirconium oxide module outlet and into zirconium oxide module effluent line 1614. The zirconium oxide module 1604 can be flushed with any volume of water required to ensure that the disinfectant is removed.

The zirconium oxide pumps 1611 and 1612 can pump fluid from base source 1608 to zirconium oxide module 1604. The base source 1608 can contain hydroxide ions to recharge zirconium oxide module 1604. The hydroxide ions can flow through zirconium oxide module 1604 and into zirconium oxide module effluent line 1614. The base source 1608 can be any suitable basic solution capable of replacing phosphate and other anions bound to the zirconium oxide with hydroxide ions. The hydroxide base can be any suitable base such as sodium hydroxide. One non-limiting example is sodium hydroxide having a concentration between 0.5 M and 2.0 M. Another non-limiting example is sodium hydroxide having a concentration at 90% or greater than 2% of the concentration of the recharging solution. A final rinse of the zirconium oxide module 1604 can be performed by pumping water through the zirconium oxide recharging flow path 1602 and zirconium oxide module 1604.

Effluent from zirconium phosphate recharging flow path 1601 can neutralize, either completely or in part, the effluent from zirconium oxide recharging flow path 1602, and vice versa. Zirconium phosphate effluent line 1613 can be fluidly connected to zirconium oxide effluent line 1613 at an effluent line junction 1616 joining drain line 1615, which fluidly connects to drain 1617. A static mixer can be used at or downstream of the effluent line junction 1616 to mix zirconium phosphate effluent with zirconium oxide effluent.

Zirconium phosphate effluent line 1613 and zirconium oxide effluent line 1614 can be connected to a common reservoir for storage and disposal of the combined effluent. The common reservoir receives and collects the zirconium phosphate and zirconium oxide effluents together. The collected effluents can be drained after appropriate volumes of each effluent have been added to achieve neutralization. A common reservoir can allow for neutralization of the zirconium phosphate and zirconium oxide effluents without synchronizing the recharging processes. A single common reservoir could also be sized to support multiple rechargers.

Alternatively, the two fluid streams may be mixed through fluid line mixing at the effluent line junction 1616. The composition and flow rates of the zirconium phosphate and zirconium oxide effluents can be monitored with sensors. Data from the sensors can determine if the combined effluent in drain line 1615 is safe for disposal into a drain. One non-limiting example of safe is an effluent having a pH in the range of 5-9. Either zirconium phosphate effluent line 1613 or zirconium oxide effluent line 1614 can be connected simultaneously or independently to a waste reservoir (not shown) for disposal. Additional pH or conductivity sensors can be positioned downstream of the junction 1616 to monitor and ensure safe disposal. Drain line 1615 can also be connected to a common waste reservoir for storage and disposal of effluent. The common reservoir receives and collects the zirconium phosphate and zirconium oxide effluents together. The collected effluents can be drained after appropriate volumes of each effluent have been added to achieve neutralization. A common waste reservoir advantageously allows for neutralization of the zirconium phosphate and zirconium oxide effluents without synchronizing the recharging processes.

During recharging, fluid can be passed through the zirconium phosphate module 1603 and/or the zirconium oxide module 1604 opposite to a flow direction used during dialysis. For example, the zirconium phosphate module inlet can be used as the zirconium phosphate module outlet during dialysis, and the zirconium phosphate module outlet can be the zirconium phosphate module inlet during dialysis. Pumping the recharging fluid through the modules in the opposite direction relative to dialysis can improve the efficiency of the recharging process.

The zirconium phosphate recharging flow path 1601 or zirconium oxide recharging flow path 1602 can independently recharge zirconium phosphate or zirconium oxide. For example, a single flow path fluidly connecting zirconium phosphate module 1603 to each of the water source 1605, brine source 1606 and/or acid source (not shown), and disinfectant source 1607 can independently recharge the zirconium phosphate module 1603. Similarly, a single flow path fluidly connecting zirconium oxide module 1604 to each of the water source 1605, disinfectant source 1607, and base source 1608 can independently recharge the zirconium oxide module 1604.

The water source 1605, brine source 1606, disinfectant source 1607, and base source 1608 can recharge one or more reusable sorbent module of various sizes either in a single recharger or in multiple rechargers connected together. The amount of water, brine, disinfectant, and base can depend on the concentration of each of the recharging solutions, the size of the reusable sorbent modules, the amount of cations/anions removed, and the flow rate used to pass the solutions through the reusable modules. The amount of brine solution required can depend on the temperature to which the brine solution is heated. For example, a brine solution having between 2.5 M and 4.9 M sodium chloride, between 0.3 M and 1.1 M sodium acetate, and between 0.2 M and 0.8 M acetic acid at between 70° C. and 90° C. requires between 4.2-6.2 L of brine to recharge a zirconium phosphate module containing between 2 kg and 3.2 kg of zirconium phosphate loaded with 2 to 3 moles of ammonium, calcium, magnesium and potassium. The brine solution should have a volume of at least between 4.2 and 6.2 L and delivered at a flow rate of between 100 and 300 mL/min. A single brine source can be connected to multiple rechargers, or can recharge multiple zirconium phosphate sorbent modules in a single recharger. The brine source can have a larger volume from 1-100× or greater to ensure that the brine source need not be refilled each time a zirconium phosphate is recharged. For a zirconium oxide module having between 220 and 340 g of zirconium oxide loaded with 200 mmols of phosphate, a base source having between 0.5 and 2.0 M sodium hydroxide and a flow rate between 30 and 150 mL/min requires between 1 and 4.0 L of base. The base source can be at least between 1 and 4.0 L in volume. For recharging multiple zirconium oxide modules, a larger base source can be used.

One of skill in the art will understand that FIG. 16 provides a non-limiting generalized view of the recharging flow paths. Additional valves and fluid lines can be included to control the movement of the recharging solutions through the recharging flow paths. Alternative flow path arrangements are within the scope of the invention.

One skilled in the art will understand that various combinations and/or modifications and variations can be made in the described systems and methods depending upon the specific needs for operation. Features illustrated or described as being part of an aspect of the invention may be used in the aspect of the invention, either alone or in combination.

I claim:

1. A recharger, comprising:
   at least one sorbent module receiving compartment for receiving at least one sorbent module;
   at least one recharger connector affixed to an outer surface of the recharger and fluidly connectable to a fluid line connected to a second recharger or to a second recharger, wherein the second recharger comprises at least one sorbent module receiving compartment for receiving at least one sorbent module;
   wherein the recharger connector is fluidly connected to at least a first recharging flow path in the recharger and a second recharging flow path in the second recharger.

2. The recharger of claim 1, wherein the recharging flow path is selected from the group consisting of a zirconium phosphate recharging flow path comprising a zirconium phosphate module inlet and a zirconium phosphate module outlet; a zirconium oxide recharging flow path comprising a zirconium oxide module inlet and zirconium oxide module outlet; an activated carbon recharging flow path comprising an activated carbon module inlet and an activated carbon module outlet, an alumina recharging flow path comprising an alumina module inlet and an alumina module outlet, and combinations thereof.

3. The recharger of claim 1, wherein the recharger connector is fluidly connectable to a first end of a fluid connector; and wherein a second end of the fluid connector is fluidly connectable to a recharger connector of a second recharger.

4. The recharger of claim 1, wherein the recharger comprises a zirconium phosphate recharging flow path comprising a zirconium phosphate module inlet and a zirconium phosphate module outlet and a zirconium oxide recharging flow path comprising a zirconium oxide module inlet and zirconium oxide module outlet; and further comprising a drain line fluidly connectable to one or both of the zirconium phosphate module outlet and zirconium oxide module outlet.

5. The recharger of claim 4, wherein the drain line is fluidly connectable to a drain line of a second recharger.

6. The recharger of claim 4, wherein the drain line is fluidly connectable to a common reservoir; wherein the common reservoir is fluidly connectable to a drain line of a second recharger.

7. The recharger of claim 1, comprising multiple recharger connectors.

8. The recharger of claim 1, wherein the recharger connector is fastenable to a recharger connector of a second recharger.

9. A recharging system, comprising:
   at least one recharger having at least one receiving compartment for receiving a rechargeable dialysis component; at least one inlet and outlet; the inlet fluidly connectable to a recharging flow path; the recharger in fluid communication with a fluid line;
   at least one recharging solution source selected from the group consisting of a disinfectant source, a water source, a brine source, a base source, and an acid source; the recharging solution source fluidly connected to a fluid line; the recharging solution source in fluid communication with the fluid line; and at least one recharger connector affixed to an outer surface of the recharger, the recharger connector in fluid communication with the fluid line; and a second recharger connector affixed to an outer surface of the recharger; the second recharger connector fluidly connectable to a recharger connector of a second recharger having at least one sorbent module receiving compartment for receiving at least one sorbent module.

10. The recharging system of claim 9, wherein the second recharger connector is directly connectable to the recharger connector of the second sorbent recharger.

11. The recharging system of claim 9, wherein the second recharger connector is fluidly connectable to a fluid line; the fluid line fluidly connectable to the recharger connector of the second sorbent recharger.

12. The recharging system of claim 9, wherein the fluid line is fluidly connectable to both a zirconium phosphate recharging flow path and a zirconium oxide recharging flow path.

13. The recharging system of claim 9, wherein the fluid line comprises at least two recharger connectors, each of the at least two recharger connectors fluidly connectable to a sorbent recharger.

14. The recharging system of claim 9, wherein the recharger connector is a sealable connector; wherein the recharger connector is sealed and/or fluidly connected to a second sorbent recharger.

15. The recharging system of claim 9, further comprising a drain line fluidly connected to at least a first sorbent recharger and a second recharger.

16. The recharging system of claim 15, wherein the drain line is fluidly connected to a drain.

17. The recharging system of claim 15, wherein the drain line is fluidly connected to a common reservoir.

* * * * *